(12) United States Patent
Winslow et al.

(10) Patent No.: US 8,840,672 B2
(45) Date of Patent: Sep. 23, 2014

(54) SPRING BASE GLENOSPHERE

(71) Applicant: Biomet Manufacturing, LLC, Warsaw, IN (US)

(72) Inventors: Nathan A. Winslow, Warsaw, IN (US); John M. McDaniel, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/089,004

(22) Filed: Nov. 25, 2013

(65) Prior Publication Data
US 2014/0081407 A1   Mar. 20, 2014

Related U.S. Application Data

(63) Continuation of application No. 13/115,548, filed on May 25, 2011, now Pat. No. 8,591,591.

(51) Int. Cl.
*A61F 2/40* (2006.01)
*G06K 9/46* (2006.01)
*G06K 9/00* (2006.01)
*A61F 2/30* (2006.01)

(52) U.S. Cl.
CPC ............ *A61F 2/4014* (2013.01); *G06K 9/4623* (2013.01); *A61F 2002/30607* (2013.01); *A61F 2002/30369* (2013.01); *A61F 2002/4085* (2013.01); *A61F 2002/30378* (2013.01); *A61F 2002/30563* (2013.01); *A61F 2/4081* (2013.01); *G06K 9/00604* (2013.01); *A61F 2002/30354* (2013.01); *A61F 2002/30332* (2013.01); *A61F 2002/3037* (2013.01)
USPC ...................... 623/19.11; 623/19.12

(58) Field of Classification Search
CPC ........... A61F 2/4081; A61F 2002/4085; A61F 2002/4022
USPC .................. 623/19.11, 19.12, 19.13
See application file for complete search history.

(56) References Cited

U.S. PATENT DOCUMENTS

2004/0220673 A1* 11/2004 Pria ............................ 623/19.12

* cited by examiner

*Primary Examiner* — Bruce E Snow
*Assistant Examiner* — Brian Dukert
(74) *Attorney, Agent, or Firm* — Harness, Dickey

(57) ABSTRACT

A method for implanting a reverse modular humeral implant into a humerus that includes a natural humeral shaft and a natural humeral head. The implant includes a humeral stem implantable into the natural humeral shaft, and an adapter couplable to the humeral stem, the adapter including an anchoring projection configured to be coupled to a convex bearing.

20 Claims, 6 Drawing Sheets

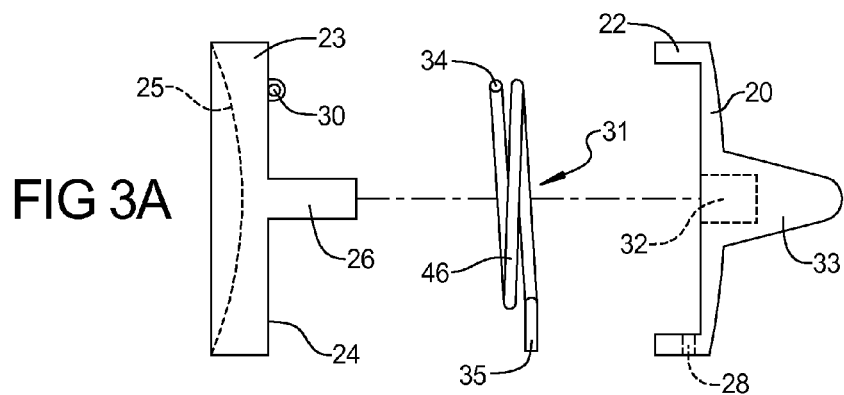
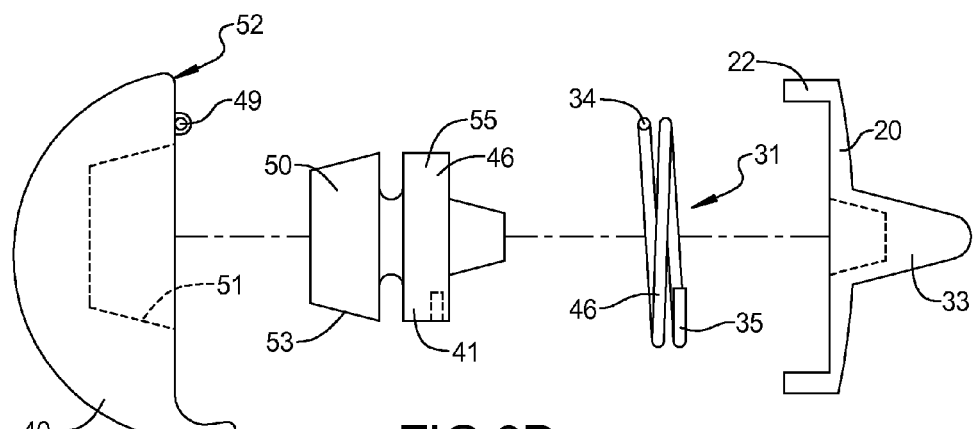
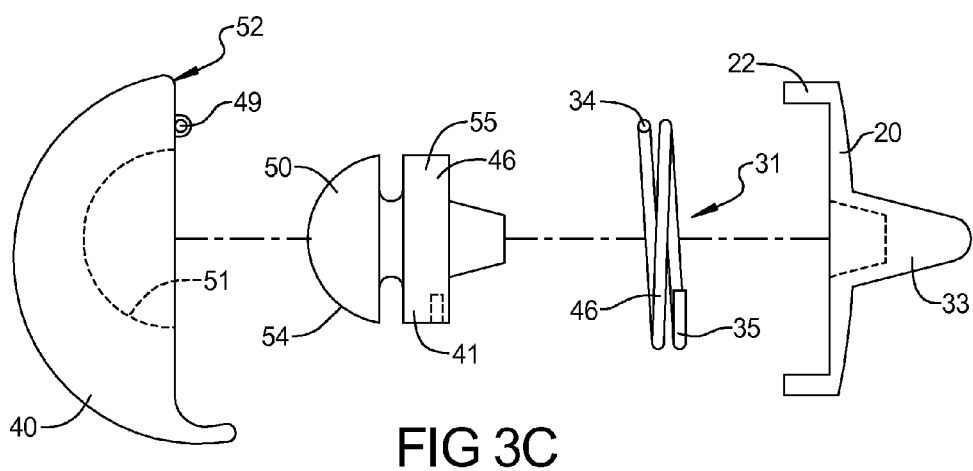

under of US 8,840,672 B2

SPRING BASE GLENOSPHERE

CROSS-REFERENCE TO RELATED APPLICATIONS

This application is a continuation of U.S. patent application Ser. No. 13/115,548 filed on May 25, 2011. The entire disclosure of the above application is incorporated herein by reference.

FIELD

The present disclosure relates to a humeral prosthesis for total shoulder joint replacement and generally includes a prosthetic coupling mechanism, an annular spring member, and a prosthetic head which replaces a portion of the humeral joint.

BACKGROUND

This section provides background information related to the present disclosure which is not necessarily prior art.

It is not uncommon for the exterior surface of the humeral head to be damaged or defective. Conventionally, a variety of humeral head resurfacing implants exist for repairing humeral head surfaces. While conventional humeral head resurfacing implants are suitable for their intended uses, such implants are subject to improvement.

Conventional humeral implants fail to accommodate patients having inadequate skeletal structure during an impact situation. Specifically, conventional implants do not permit relative movement between the components or the absorption of impact energy. These impacts are often off axis and have complex loading parameters.

To overcome these deficiencies, reverse shoulders using a glenosphere have been used. These reverse shoulders may be susceptible to impacts when a patient inadvertently falls, impacting the prosthetic. Thus, there is a need for a humeral implant that permits proper articulation dynamics, while accepting impact loads.

SUMMARY

This section provides a general summary of the disclosure, and is not a comprehensive disclosure of its full scope or all of its features. Various aspects of the teachings provide a modular humeral implant and associated kit and method for implantation into a shoulder joint that includes a natural humeral shaft and a natural humeral head and glenoid.

A modular reverse shoulder prosthetic is taught. The reverse shoulder prosthetic can have a glenoid tray configured to be implanted into a resected glenoid. The tray can have an opposed bearing mounting surface defining a coupling taper therein. A bearing coupling member is provided which is configured to engage the bearing mounting surface. A depending spring member is provided that is configured to be disposed radially about the bearing coupling member. The spring is coupled to a glenosphere bearing and the tray or the coupling member.

According to alternate teachings, the shoulder prosthetic can have a glenoid tray configured to be implanted into the resected glenoid. The tray can have a glenoid interface surface with a depending coupling stem and an opposed bearing mounting surface. The bearing mounting surface defines a coupling aperture having a coupling taper. A spring member is first disposed within a cavity defined by the glenoid tray, and is coupled to a glenosphere and defines an aperture which can annularly accept a bearing coupling member. The bearing coupling member is disposed within the spring member aperture.

According to alternate teachings, the glenoid tray can define a glenoid tray spring coupling ledge configured to annularly support the spring member when the bearing coupling member is engaged with the spring and the glenoid tray. The glenosphere head member is translatable with respect to the bearing coupling member.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The drawings described herein are for illustrative purposes only of selected embodiments and not all possible implementations, and are not intended to limit the scope of the present disclosure.

FIGS. 3A-3C are side exploded views of a humeral implant subassembly using the coupling mechanism, spring, and tray according to the present teachings;

DETAILED DESCRIPTION

Example embodiments will now be described more fully with reference to the accompanying drawings.

Figure 1:
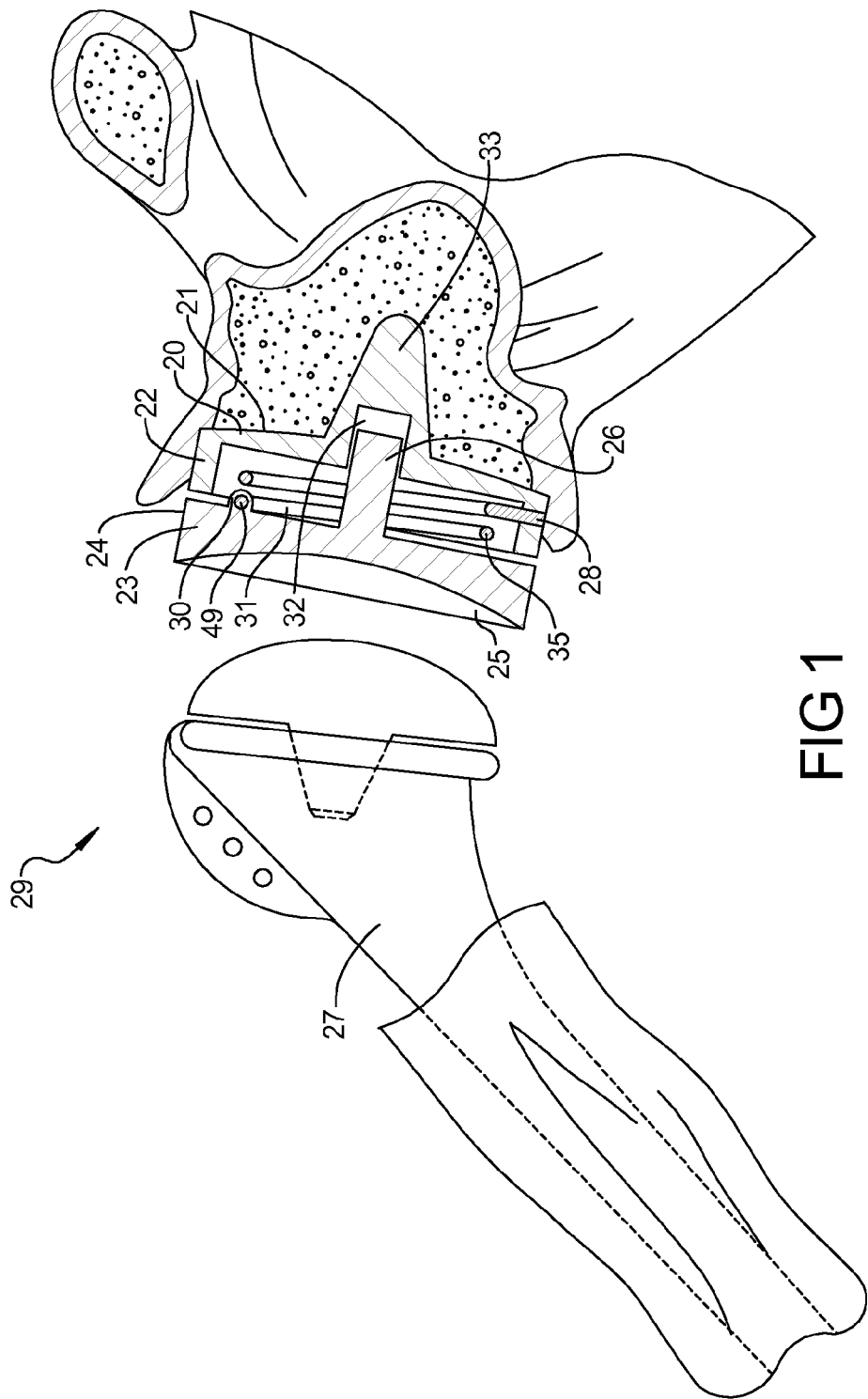
FIG. 1 is a cross-sectional view of a humeral implant according to the present teachings.

FIG. 1 represents a cross-sectional view of the shoulder system 29 according to the present teachings. The system 29 utilizes the glenoid coupling member or glenoid tray 20 to couple a shoulder bearing 23 to the prepared glenoid. Disposed within the glenoid tray 20 is the shoulder bearing 23 having a mounting interface surface 24 and concave bearing surface 25. The concave bearing surface 25 is configured to interface with the articulating surface of a humeral prosthetic 27. The mounting interface surface 24 can have an intermediate depending piston 26. The intermediate depending piston 26 can be fixed to mounting interface surface 24 or, as described below, to the glenoid tray 20.

Operably disposed between the shoulder bearing 23 and the glenoid tray 20 is an annular spring member 35. The spring member 35 functions to couple the bearing 23 to the glenoid tray 20. In this regard, the spring member 35 functions to limit or constrain movement of the shoulder bearing 23 with respect to the glenoid tray 20. Additionally, the spring member 35 functions to absorb impacts or forces applied onto the bearing surface 25. The annular spring member 35 has a first end fixably coupled to an aperture 28 formed within the glenoid tray 20. At its second end, the spring member 35 is fixably coupled to an aperture 30 formed on the interface side of the bearing 23.

It is envisioned the intermediate depending piston 26 fixed to the mounting interface surface 24 can be slidably accepted by the cylindrical aperture 32 defined within the glenoid tray 20. The intermediate depending piston 26 and cylindrical aperture 32 can be sized and toleranced so that the interface between the intermediate depending piston 26 and aperture 32 functions as a fluid damper. The aperture 32 can be formed in a tray coupling stem 33.

The coiled spring member 35 can define a central through bore 31 which annularly surrounds the intermediate depending piston 26. It is envisioned that the spring member 35 can be positioned within a cavity defined by a fixation edge 22 of the glenoid tray 20. Alternatively, the spring member 35 may be incorporated into a cavity (not shown) defined by the bearing 23 mounting interface surface 24. In addition, the spring member 35 may be sized and configured to be located within the cylindrical aperture 32 in order to impart force upon the intermediate depending piston 26.

Figure 2:
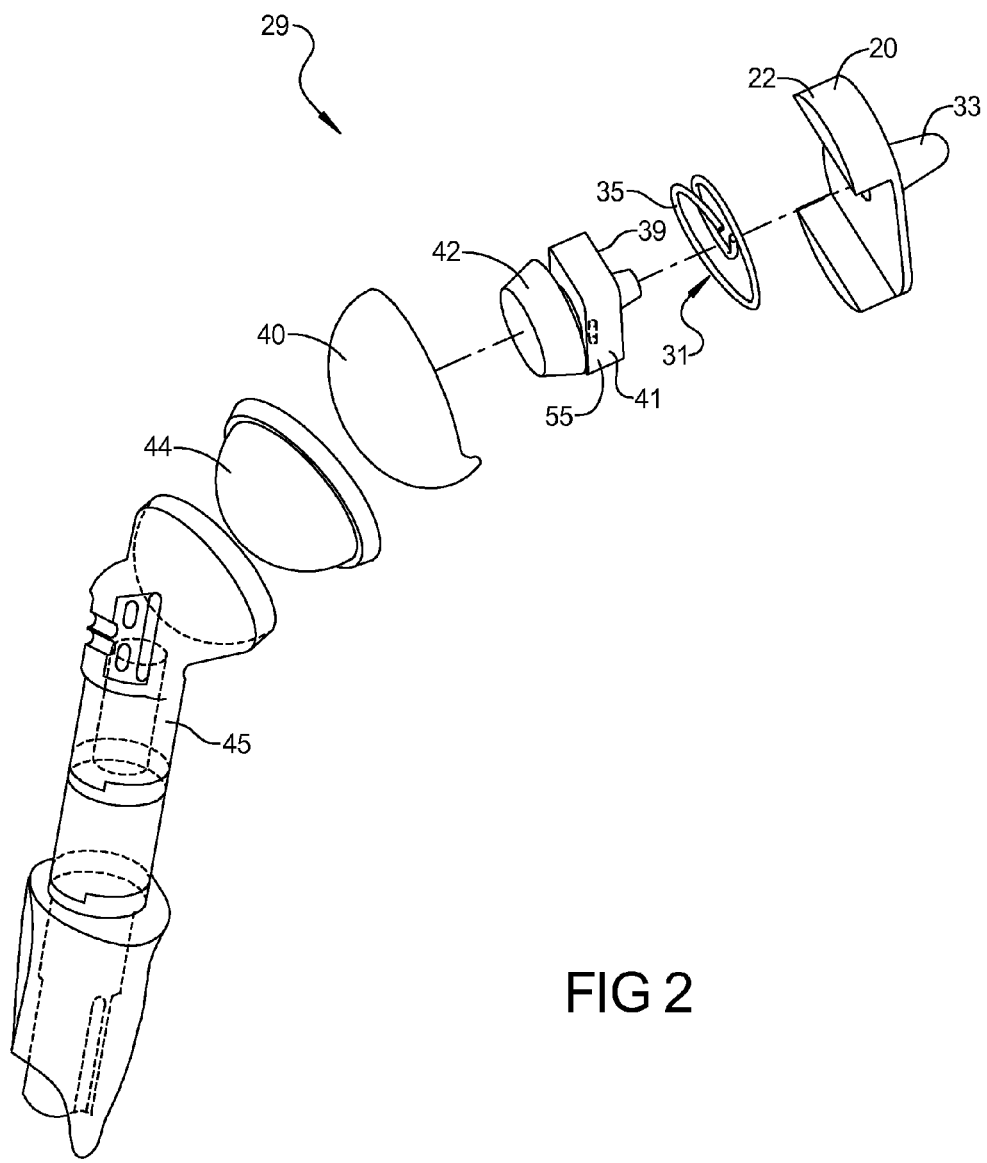
FIG. 2 is an exploded view of an alternate reverse humeral implant according to the present teachings.

As shown in FIG. 2, a glenosphere head 40 can be coupled to the glenoid tray 20 using a bearing coupling member or intermediary coupling member 41. Disposed about the intermediary coupling member 41 is a spring member 35, which can be coupled between the intermediary coupling member 41 and the head 40. The coupling member 41 is non-rotatably, but floatably disposed within the glenoid tray 20 using, by way of non-limiting example, the coupling taper 42. In this regard, the coupling taper 42 is inserted into a bore defined within the glenoid tray or support structure 20.

The head 40 is configured to be coupled to a cup member bearing 44 fixed to the stem 45. As further described below, the head 40 is coupled directly to the glenoid tray 20 or to the glenoid tray 20 through the intermediary coupling member 41 using the spring member 35. The spring member 35 is fixably or rotatably coupled to the head 40 and the intermediary coupling member 41. The taper 42 is configured to loosely couple to a taper in the head 40. In this regard, the taper 42 can be a non-locking taper.

FIGS. 3A and 3B represent exploded cross-sectional views of the shoulder components according to the present teachings. FIG. 3A depicts the components shown in FIG. 1. As shown, the spring coupling apertures defined by the bearing 23 or the glenoid tray 20 can be generally parallel to the interface surfaces of both the bearing 23 and the glenoid tray 20.

FIGS. 3B and 3C represent reverse shoulder components having an intermediary coupling member 41. The intermediary coupling member 41 has a head bearing surface 50 which is translationally coupled to a corresponding surface 51 defined within the head. The head bearing surface 50 is configured to transfer applied loads onto the head bearing surface 50 through the coupling member 41 and into the glenoid tray 20. The head bearing surface 50 can be a non-locking taper 53 or a spherical bearing surface 54.

The spring coupling member 35 has an exterior surface 46 having a generally fixed radius of curvature about the centerline defining the coupling member 41. The spring coupling member 35 generally can present one and a half rotations which has a cross-sectional area smaller than the cross-sectional area of the head. As shown in FIGS. 3B and 3C, the ledge portion 52 of the head 40 is configured to annularly enclose the spring member 35.

Figure 4:
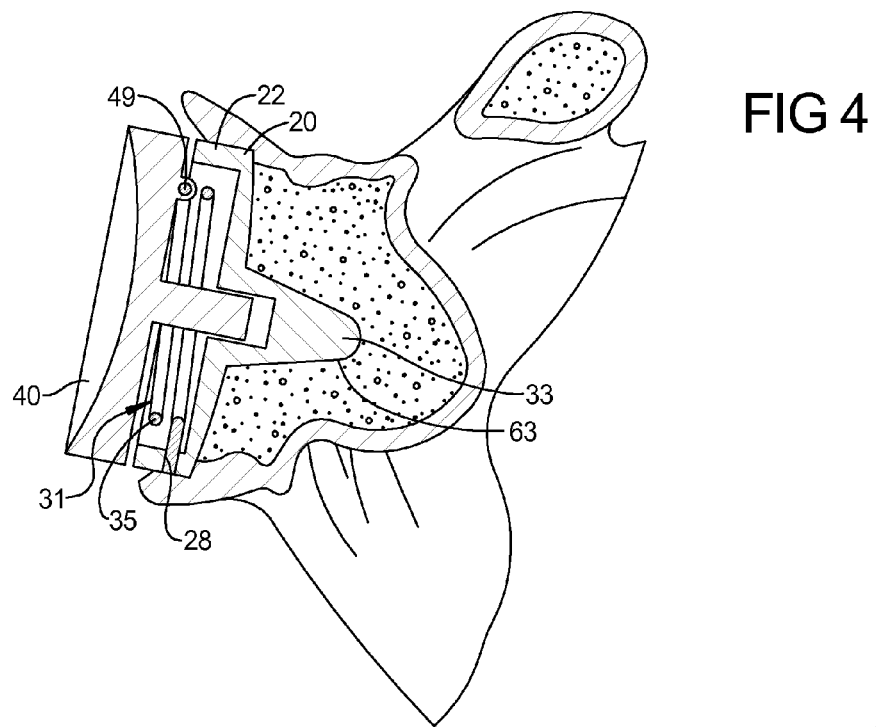
FIG. 4 is an assembled view of the prosthetic according to the prosthetic of FIG. 3A.
Figure 5:
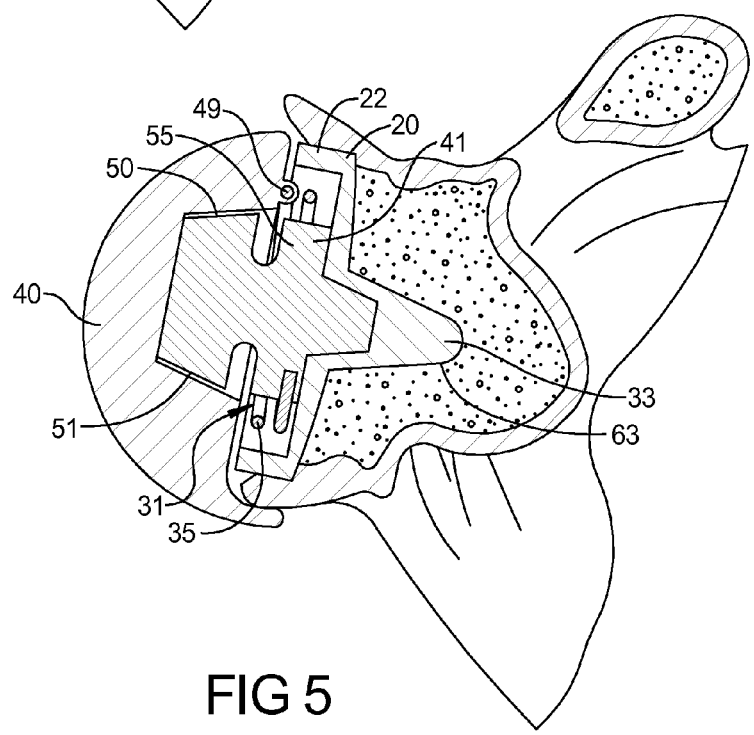
FIG. 5 represents an assembled view of the prosthetic of FIG. 3B.
Figure 6:
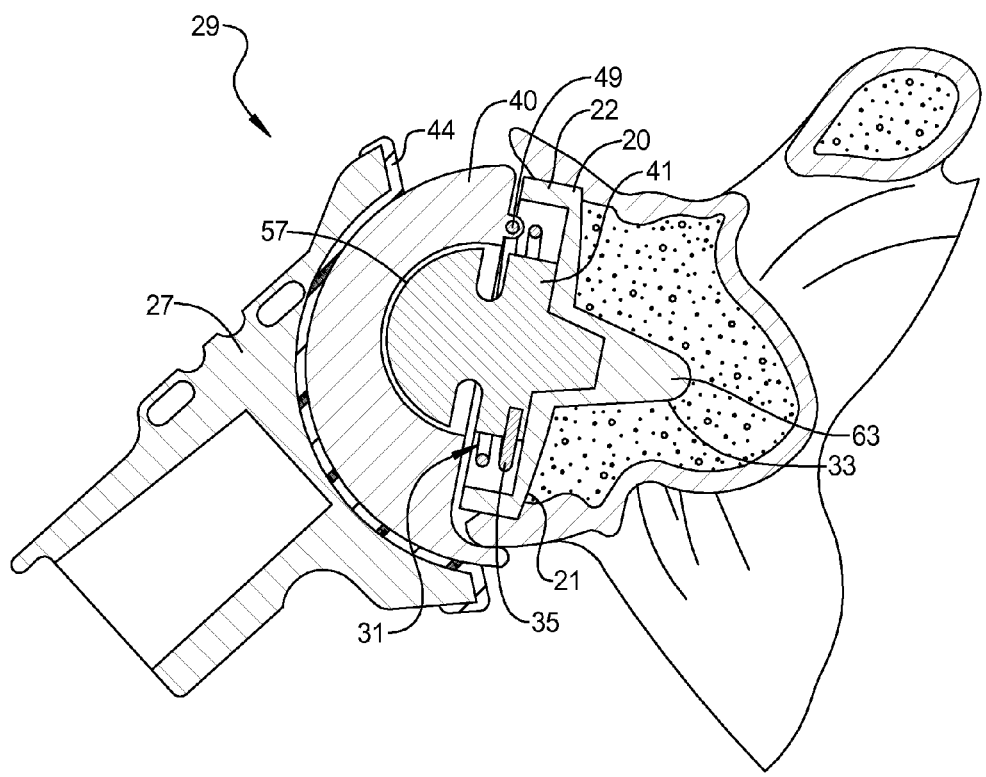
FIG. 6 represents an assembled view of the prosthetic of FIG. 3C.

FIGS. 4-6 represent cross-sectional views of the implantation of the shoulder components shown in FIGS. 1-3C. After the resection of the glenoid, an aperture 63 can be formed within the glenoid to accept a tray coupling stem 33. After coupling the glenoid tray 20 to the resected glenoid, the spring member 35 can be coupled to the glenoid tray 20 or the coupling member 41.

After coupling the spring member 35 to the glenoid tray 20 or the coupling member 41, the coupling member 41 (if used) can be coupled to a coupling taper defined in the glenoid tray 20. The second end 34 of the spring member 35 can then be coupled into the spring coupling aperture 49 formed in the mating surface of the head 40.

Figure 7:
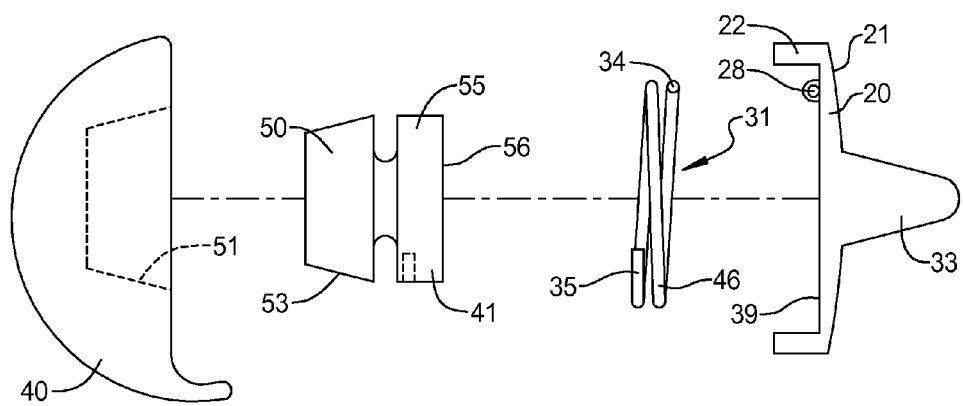
FIG. 7 represents an alternate glenosphere prosthetic.

As shown in FIG. 7, the glenoid tray 20 can be flexibly coupled to the head 40. In this regard, the coupling member 41 can be fixably coupled to the head 40 by the coupling surface 53. The coupling member 41 has a flat surface 56 which slidably interfaces with a planar interface surface 39. The floating head 40 and coupling member 41 are movably fixed to the glenoid tray 20 through the spring member 35. As with all of the examples, the head can be moveable with respect to the glenoid tray, the bearing coupling member, or a portion of the spring when the head is subjected to forces.

Figure 8:
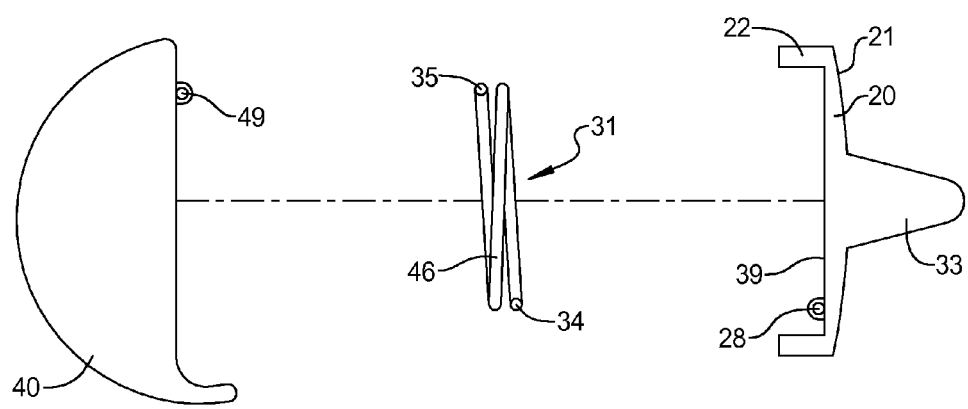
FIG. 8 represents an alternate glenospherical prosthetic.

As seen in FIG. 8, the head 40 can be coupled directly to the glenoid tray 20 using only the coupling spring member 35. As described above, the coupling spring can be fixably coupled at the coupling apertures.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of implanting a shoulder prosthetic, the method comprising:
    implanting a glenoid tray into a resected glenoid, the glenoid tray having a glenoid interface surface, an opposed bearing mounting surface, and a stem extending from the glenoid interface surface along a longitudinal axis in a direction away from the opposed bearing mounting surface;
    providing an articulating bearing;
    engaging the bearing mounting surface with an interface surface of a bearing coupling member;
    mating a bearing coupling surface of the bearing coupling member to a corresponding surface on the articulating bearing such that the bearing coupling member extends along the longitudinal axis; and
    coupling a spring to the articulating bearing and one of the glenoid tray and the bearing coupling member such that the bearing coupling member remains movable along the longitudinal axis with respect to at least one of the articulating bearing and the glenoid tray after implantation of the prosthetic.

2. The method according to claim 1, comprising:
    positioning the spring within a cavity of the bearing mounting surface of the glenoid tray, wherein the glenoid tray defines an aperture spaced apart from the cavity and extending along the longitudinal axis into the stem and the bearing coupling member is at least partially disposed in the aperture.

3. The method according to claim 2, comprising:
    positioning the bearing coupling member within an inner bore of the spring and engaging the bearing coupling member with the glenoid tray.

4. The method according to claim 3, wherein the articulating bearing is translatable with respect to the bearing coupling member.

5. The method according to claim 2, comprising:
    fixedly locking the bearing coupling member to the glenoid tray.

6. The method according to claim 1, wherein the articulating bearing is translatable with respect to the glenoid tray.

7. The method according to claim 1, wherein the bearing coupling surface is spherical and the articulating bearing is translatable with respect to the glenoid tray in a direction parallel to the bearing mounting surface.

8. A method of implanting a shoulder prosthetic, the method comprising:
    providing an articulating bearing member;
    implanting a glenoid tray into a resected glenoid, the glenoid tray having a glenoid interface surface, an opposed bearing mounting surface, and a stem extending from the glenoid interface surface along a longitudinal axis, the bearing mounting surface defining an aperture extending along the longitudinal axis and within the stem;
    positioning a spring member defining a spring member aperture adjacent the glenoid tray;
    coupling the spring member to a bearing coupling member; and
    at least partially disposing the bearing coupling member within the spring member aperture such that the bearing coupling member remains movable along the longitudinal axis with respect to at least one of the articulating bearing member and the glenoid tray after implantation of the prosthetic.

9. The method according to claim 8, comprising:
    coupling the spring member to a coupling ledge of the bearing coupling member.

10. The method according to claim 9, wherein the articulating bearing member is translatable with respect to the bearing coupling member from a first position to a second position.

11. The method according to claim 8, wherein the bearing coupling member has a depending locking surface configured to be received in the aperture and further has a bearing coupling side having a coupling surface configured to mate to a corresponding complementary surface on the articulating bearing member.

12. The method according to claim 8, comprising:
    fixedly coupling the articulating bearing coupling member to the glenoid tray.

13. The method according to claim 8, wherein the articulating bearing member has a convex articulating surface and the bearing coupling member is translatable with respect to the glenoid tray in a direction parallel to the bearing mounting surface.

14. A method of implanting a prosthetic, the method comprising:
    providing a glenosphere defining an articulating surface and a coupling surface;
    implanting a glenoid tray into a resected surface, the glenoid tray defining an aperture, a bearing mounting surface, and an opposed glenoid interface surface including a stem extending therefrom along a longitudinal axis in a direction away from the bearing mounting surface;

disposing a spring member within a cavity of the bearing mounting surface;

positioning at least a portion of a bearing coupling member within an aperture defined by the spring member, the bearing coupling member having an interface surface configured to engage the bearing mounting surface; and coupling the bearing coupling member to the glenoid tray such that the bearing coupling member remains movable along the longitudinal axis with respect to at least one of the glenosphere and the glenoid tray after implantation of the prosthetic.

15. The method according to claim 14, comprising:
interfacing a spherical convex surface of the articulating surface of the glenosphere with a concave bearing.

16. The method according to claim 14, wherein the bearing coupling member has a spherical bearing coupling surface.

17. The method according to claim 14, wherein the glenosphere is translatable with respect to a portion of the spring.

18. The method according to claim 14, wherein the glenosphere is translatable with respect to the bearing coupling member.

19. The method according to claim 14, comprising:
fixedly coupling the bearing coupling member to the glenoid tray.

20. The method according to claim 14, comprising:
coaxially aligning the cavity, aperture, stem, and bearing coupling member.

* * * * *